(12) United States Patent
Oda et al.

(10) Patent No.: US 6,376,213 B1
(45) Date of Patent: Apr. 23, 2002

(54) METHOD FOR DECOMPOSING POLYESTERS CONTAINING AROMATIC MOIETIES, A DENIER REDUCTION METHOD OF FIBER, AND MICROORGANISMS HAVING ACTIVITY OF DECOMPOSING THE POLYESTER

(75) Inventors: Kohei Oda, Izumi; Yoshiharu Kimura, Ohmihachiman, both of (JP)

(73) Assignee: Kyoto Institute of Technology, Kyoto (JP)

( * ) Notice: Subject to any disclaimer, the term of this patent is extended or adjusted under 35 U.S.C. 154(b) by 0 days.

(21) Appl. No.: 09/353,445

(22) Filed: Jul. 14, 1999

(30) Foreign Application Priority Data

Nov. 10, 1998 (JP) ............................................. 10-319251

(51) Int. Cl.[7] .............................. C12P 39/00; C12P 7/62; C12N 1/16; C12N 1/20
(52) U.S. Cl. .......................... 435/42; 435/135; 435/142; 435/252.1; 435/255.1; 435/830
(58) Field of Search ................................ 435/42, 252.1, 435/255.1, 135, 142, 142.1, 830

(56) References Cited

U.S. PATENT DOCUMENTS 5,053,482 A    10/1991    Tietz

FOREIGN PATENT DOCUMENTS

| DE | 44 32 161 A1 | 3/1996 |
| JP | A-7-132272 | 5/1995 |
| JP | A-8-260269 | 10/1996 |
| JP | A-9-279417 | 10/1997 |
| JP | A-10-8385 | 1/1998 |

OTHER PUBLICATIONS

Derwent Computer Abstract Jun. 1996–357085 JP 08140666.*
Derwent Computer Abstract 1997–60145Y JP 082009354, Jun. 1996.*
"Journal of Environmental Polymer Degradation" vol. 5, 1997, pp. 81–89, Biosis Abstract 199799590343.
"Biochemical Decomposing Agent For Polyester Compounds Contain Pure Crude Lipase Or Lipase–Producing–Micoorganism—, Or Culture Product Containing Lipase, As Active Ingredient" Agency of Ind. Science and Technology, Derwent Abstract 1977–60144Y/34.
Huang et al., "Biodegradeable Polymers: Photolysis and Fungal Degradation of Poly (arylene Keto Esters)", J. Appl. Polymer Sci., vol. 25, S. 1951–1960 (1980).
"Report of the Fermentation Research Intstitute" 1992, pp. 23–32, Biosis Abstract 199294038680.
"New—Microorganisms– Used in Decomposition of Polyester(s)—decomposes Aliphatic and Aromatic Ester(s) and Metabolises Phtalic Acid" Daiichi Kogyo Seiyaku Co, Ltd., Derwent Abstract 1996–357085/36.
"Biochemical Decomposition of Polyesters by Contact with Lipase Or Lipase–Producible—Microorganism" Agency of Ind. Science and Technology, Derwent Abstract 1977–60145Y/25.

* cited by examiner

*Primary Examiner*—Herbert J. Lilling
(74) *Attorney, Agent, or Firm*—Venable; Marina V. Schneller

(57) ABSTRACT

A polyester containing aromatic moieties is contacted with microorganisms having the activity of decomposing the polyester to decompose or reduce it. Preferably, either or both of Trichosporon FERM BP-6445 or Arthrobacter FERM BP-6444 was contacted with the polyester to decompose or reduce it. A fiber made of the polyester or a cloth made of such fiber may be reduced by contacting it with the microorganisms having the activity of decomposing the polyester.

6 Claims, 9 Drawing Sheets

METHOD FOR DECOMPOSING POLYESTERS CONTAINING AROMATIC MOIETIES, A DENIER REDUCTION METHOD OF FIBER, AND MICROORGANISMS HAVING ACTIVITY OF DECOMPOSING THE POLYESTER

BACKGROUND OF THE INVENTION

1. Field of the invention

The present invention relates to a method for decomposing polyesters containing aromatic moieties, a method for reducing a fiber made of such polyesters, and microorganisms capable of decomposing fibers made of such polyesters.

2. Description of the Related Art

A law for recycling a container and wrapping was enforced in April, 1997 for reducing such wastes and the resulting environmental pollution, which has been attracting public attention. A grace period of 3 years is provided for a container and wrapping made of a plastic material, which will be under the law, necessitating a high cost for the recycling, from April, 2000. Polyethylene terephthalate, universally used for a container of soft drink and seasoning, also will be under the law. Manufacturers try to collect and recycle such container.

However, polyesters containing aromatic moieties, such as polyethylene terephtalate or polybutylene terephthalate, are finally treated by reclamation or burning-up. The burning-up process inevitably produces harmful wastes and the reclamation may produce floating wastes on water, both leading to further environmental pollution.

Therefore, a container or wrapping material made of a polymer containing aromatic moieties, and clothes and ornaments made of the polyester discharged in an apparel industry will require high costs for their recycling and should finally be treated by reclamation or burning-up. A solution for treating such materials has been demanded.

SUMMARY OF THE INVENTION

An object of the invention is to provide a method for treating a material or fiber made of a polyester containing aromatic moieties, with adverse effects on environment substantially reduced.

Another object of the invention is to apply such treating method to denier-reduction process of fiber.

The present invention provides a method for decomposing polyesters containing aromatic moieties, the method comprising:

contacting a microorganism having an activity of decomposing polyesters containing aromatic moieties with the polyester to decompose it.

The inventors succeeded in decomposing a polyester containing aromatic moieties by means of microorganisms for the first time in the globe. Although aliphatic polyesters have been known to be biodegradable, it has never been known that the polyesters containing aromatic moieties are susceptible to decomposition by microorganisms. As a result, the invention may decompose and degrade such aromatic polyesters without environmental pollution, then decomposition products with low molecular weights may be returned into a substance-recycling system in natural environment.

The inventive method for decomposing polyesters containing aromatic moieties may be applied to a container, a wrapping material, as well as a fiber and cloth, each made of such polyesters. When the wastes containing the polyesters are subjected to composts, microorganisms included in the composts rapidly decompose the polyesters into nontoxic substances. Alternatively, when the wastes containing the polyesters are reclaimed, microorganisms may be included in wastes to decompose the polyesters. Such polyester wastes, contained in the composts or the reclaimed wastes, may be partly or wholly decomposed.

An effective treatment has not been found yet to treat so called a pet-bottle (a bottle made of polyethylene terephthalate). The invention provides a method for treating such bottle without leaving further wastes in natural environment.

The other treating methods, such as reclamation and burning-up, may produce harmful substances. The inventive microorganisms capable of decomposing the polyesters may survive for a long time, even when utilizing the polyesters as a sole carbon source, thereby probably alleviating the possibility of producing harmful substances.

The inventors also succeeded in applying the inventive decomposition method for denier reduction process of the surface of fibers made of polyesters containing aromatic moieties. The inventive reducing method produces no decomposition residue, which has been inevitably produced in the previous caustic (denier) reduction method of a fiber, thereby providing technique suitable for environment. The inventive reduction method is also useful for obtaining a fiber with better fitting and appearance. For example, a cotton fiber has been treated to improve its fitting and appearance by means of cellulase derived from microorganisms. The inventive denier reduction method may also produce a fiber and cloth made of the polyesters with improved fitting and appearance. Moreover, the thus obtained fiber has small depressions, hollows and ditches or grooves on the surface formed during the reduction process, thus facilitating its dyeing.

The inventors have confirmed the activity of decomposing a polyester containing aromatic moieties, in the following microorganisms.

(1) Trichosporon FERM BP-6445
(2) Arthrobacter FERM BP-6444

A polyester containing an aromatic moiety is a polyester produced by polymerizing monomers, at least one of the monomers being an aromatic compound. Such polyester is not particularly limited. However, such polyester may preferably be a polyalkylene phthalate, isophthalate or terephthalate, more preferably be polyethylene terephthalate, polypropylene terephthalate, or polybutylene terephthalate, and most preferably be polyethylene terephthalate or polybutylene terephthalate. The polyester may be a homopolymer of an aromatic compound, or a copolymer of aromatic compounds, or a copolymer of an aromatic compound and an aliphatic compound. The aromatic compound is not limited, and preferably be alkylene terephthalate such as ethylene terephthalate, propylene terephthalate and butylene terephthalate.

These and other objects, features and advantages of the invention will be appreciated upon reading the following description of the invention when taken in conjunction with the attached drawings, with the understanding that some modifications, variations and changes of the same could be made by the skilled person in the art.

BRIEF DESCRIPTION OF THE DRAWINGS

For a better understanding of the invention, reference is made to the attached drawings, wherein.

Figure 1:
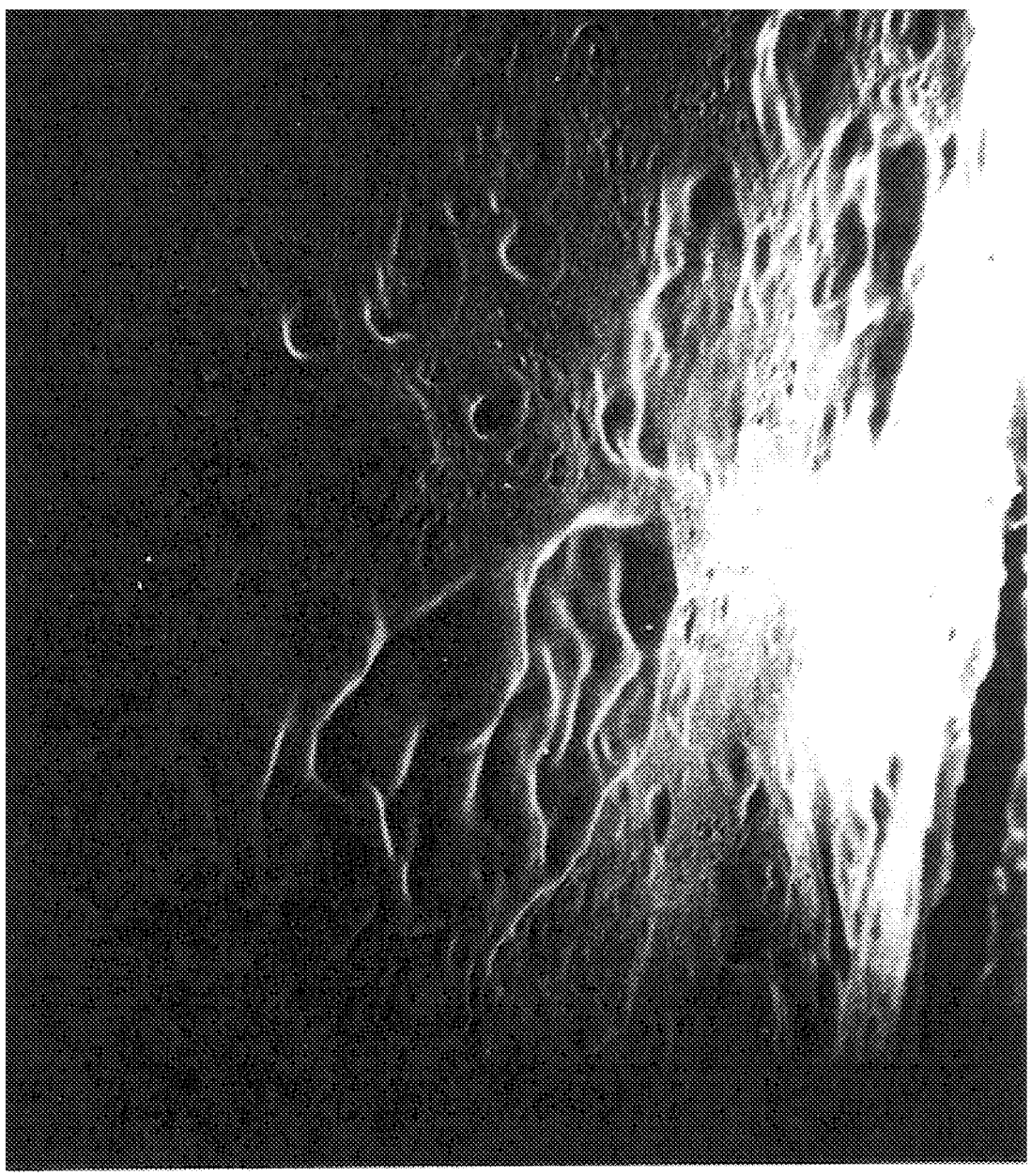
FIG. 1 is a photograph showing the surface of a fiber made of polyethylene terephthalate, taken by an electron microscope (at a magnitude of 3000), after treating it with a yeast-like microorganism having the activity of decomposing a polyester containing aromatic moiety for 30 days.

DESCRIPTION OF THE PREFERRED EMBODIMENTS (Screening of Microorganisms Capable of Decomposing a Polyester Containing an Aromatic Moiety)

The inventors found a method of cultivation for screening a micro-organism capable of decomposing a polyester containing aromatic moieties, such as polyethylene terephthalate. Polyethylene terephthalate is insoluble in water and usually has a crystalline structure. The inventor therefore added fibers, made of an amorphous or non-crystalline polyethylene terephthalate, in a medium having the following composition. Fibers were used for facilitating the judgement on whether the decomposition took place or not, in other words, the screening of a microorganism capable of decomposing the polyester. Moreover, a medium containing polyesters having aromatic moieties as a sole carbon source was used for enrichment culture.

| Used Medium | |
|---|---|
| yeast extract | 0.1% |
| ammonium sulfate | 0.2% |
| salt mixture | |
| $FeSO_4 \cdot 7H_2O$ | 0.001% |
| $CuSO_4 \cdot 5H_2O$ | 0.0001% |
| $ZnSO_4 \cdot 7H_2O$ | 0.0001% |
| $MgSO_4 \cdot 7H_2O$ | 0.0001% |

The used medium had unadjusted pH. 7 ml of the medium was contained in each tube, which was put into an autoclave and then sterilized at 120° C. for 15 minutes. Thereafter, fibers made of amorphous polyethylene terephthalate were added into each tube so that its content is made 0.2 percent. Each fiber has a diameter of 120 micrometer, a length of 5 centimeter. 12 fibers were added into each tube.

400 soil samples collected from many places in Japan were screened. A spoonful (spertel) of each soil sample was added into each medium and it was cultured at 25 to 30° C. for 1 week to select soil sample with the growing of a microorganism confirmed (first stage screening). Each soil sample was then subjected to subculture with its medium replaced every two weeks to perform enrichment culture for two months. At the end of second month, fibers made of polyethylene terephthalate were drawn from each culture medium to measure their tensile strengths using Tensilon/JTM-4L (Toyo Measuring Instruments Co. Ltd. 50 mm/min). When the tensile strength of the treated fiber is considerably reduced compared with that of an untreated fiber (blank), such fiber is further observed by means of a scanning electron microscope (Hitachi S-800). These results of the tensile strength and surface observation were considered to judge whether it is decomposition-positive or negative (second stage screening).

(Isolation of Microorganisms and its Activity of Decomposing a Polyester Containing Aromatic Moieties)

Two samples were selected from several soil samples in which the tensile strengths of the fibers were reduced. A microorganism was isolated from each of the selected two samples as a single colony. Each microorganism has the activity of decomposing a polyester containing aromatic moieties. A yeast-like microorganism was isolated from one sample and a bacterium was isolated from another. The ratio of the tensile strength of the treated fiber to that of the untreated fiber (blank) was reduced to 60 percent after 30 days, in the sample from which the yeast-like microorganism was isolated. The ratio of the tensile strength of the treated fiber to that of the untreated fiber (blank) was reduced to 92 percent after 30 days and 51 percent after 55 days, in the sample from which the bacterium was isolated.

Figure 2:
FIG. 2 is another photograph showing the surface of a fiber made of polyethylene terephthalate, taken by an electron microscope (at a magnitude of 3000), after treating it with the same yeast-like microorganism as FIG. 1 for 30 days.

FIGS. 1 and 2 show photographs of the surface of the fiber treated with the yeast-like microorganism, taken by an scanning electron microscope (at a magnitude of 3000). As shown in the FIGS. 1 and 2, many circular-shaped craters or depressions were observed on the surface of the fiber.

Figure 3:
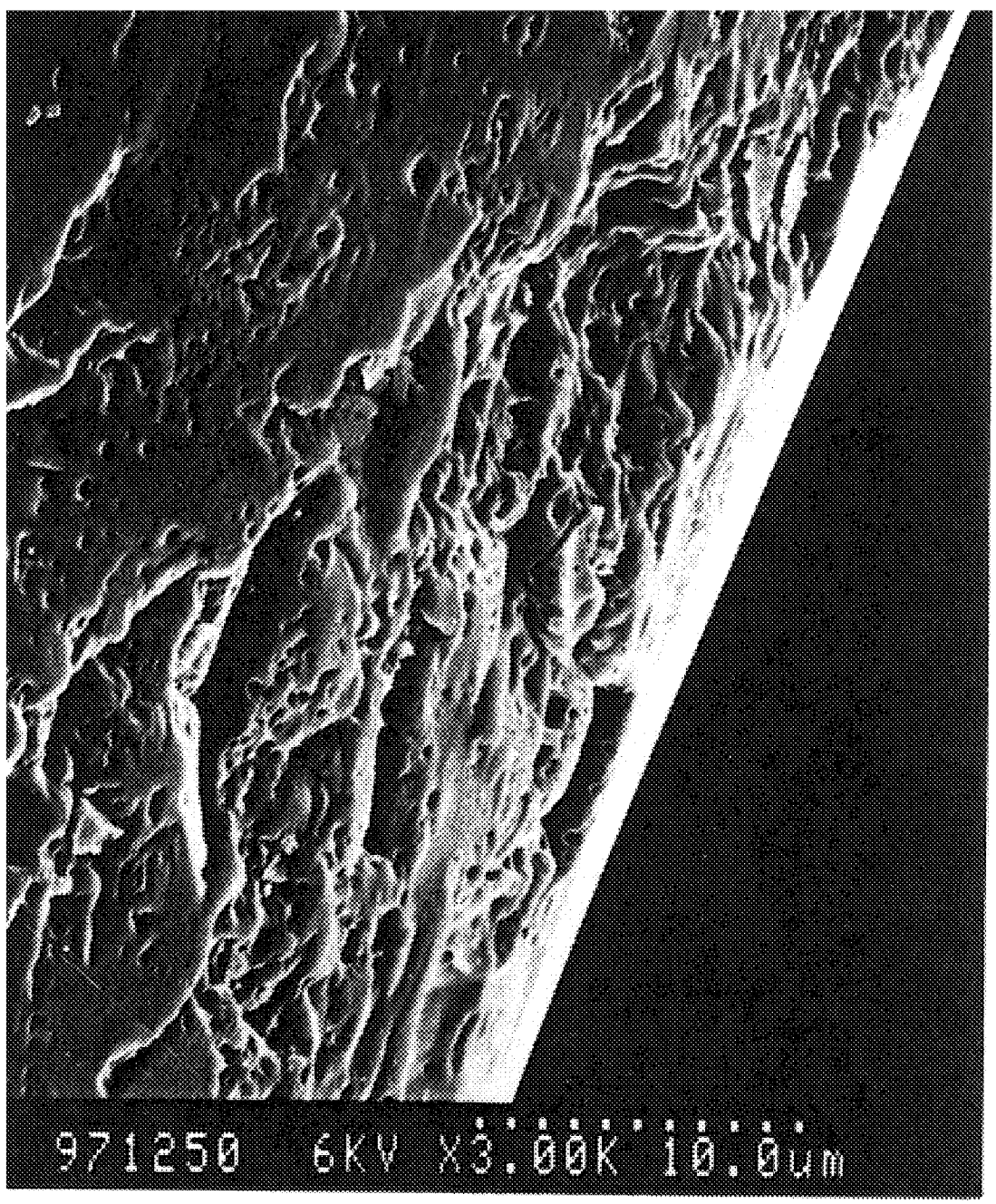
FIG. 3 is a photograph showing the surface of a fiber made of polyethylene terephthalate, taken by an electron microscope (at a magnitude of 3000), after treating it with a bacterium having the activity of decomposing a polyester containing aromatic moiety for 55 days.
Figure 4:
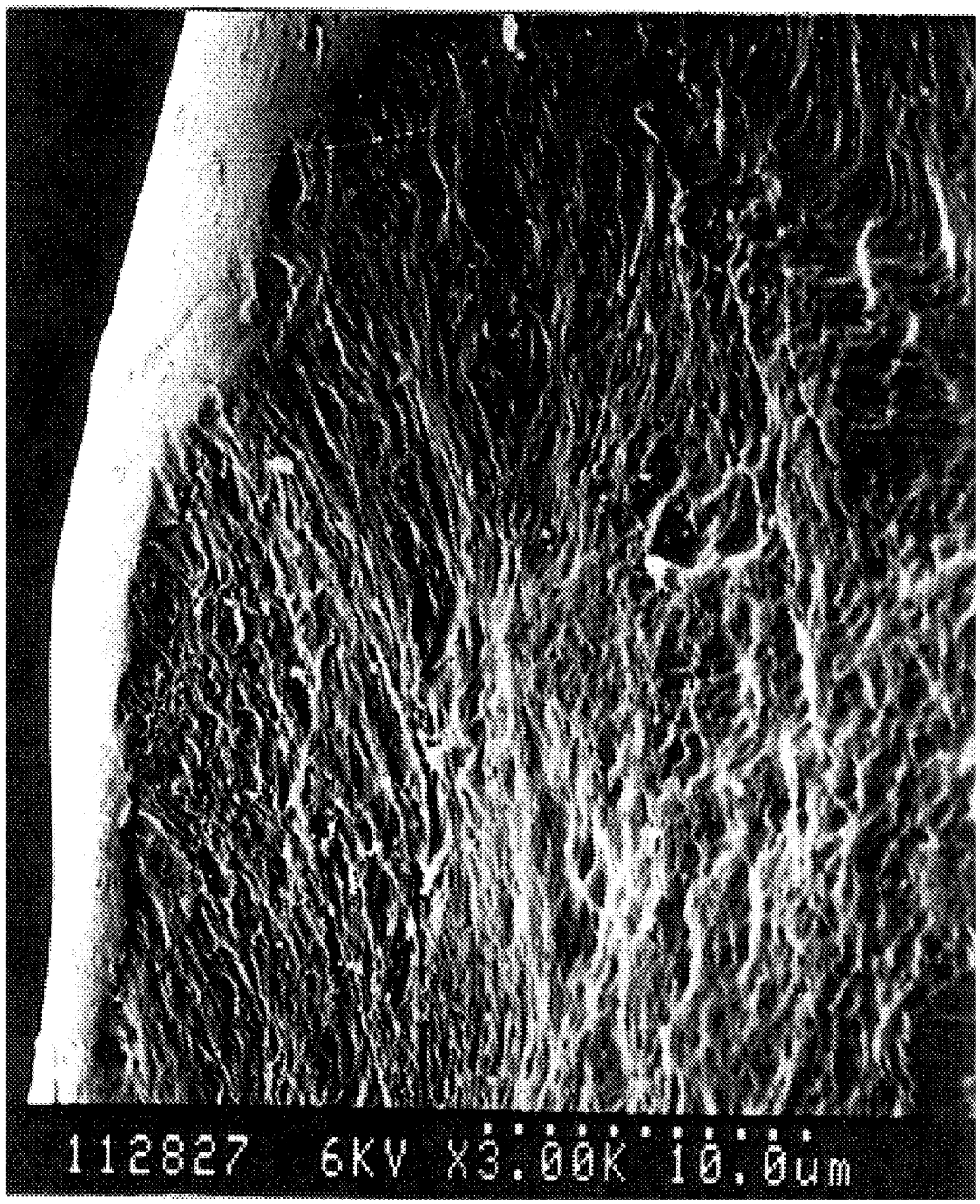
FIG. 4 is another photograph showing the surface of a fiber made of polyethylene terephthalate, taken by an electron microscope (at a magnitude of 3000), after treating it with the same bacterium as FIG. 3 for 55 days.

FIGS. 3 and 4 show photographs of the surface of the fiber treated with the bacterium by a scanning electron microscope (at a magnitude of 3000). As shown in the FIGS. 3 and 4, many eroded regions were formed and each eroded region tends to elongate in the longitudinal direction of the fiber to form small ditch or groove. Therefore, the yeast-like microorganism and bacterium may decompose the fiber to form eroded regions with characteristic patterns and morphology different form each other. Therefore, the fiber may be more effectively decomposed or reduced by contacting both of the yeast-like microorganism and bacterium together with the fiber.

(Identification of the Yeast-like Microorganism)

This microorganism belongs to Trichosporon. Its international deposit number is Trichosporon FERM BP-6445. Trichosporon is an incomplete yeast belonging to basidiomycetes which forms hyphae and oidia. The known main sources of Trichosporon are foods, intestines including that of a human, water, waste water, trees, saps or the like (reference: Kreger-van Rij, N. J. W. [The Yeasts] 1984, Elsevier Science Publishers B. V.: Barnett, J. A., Payne, R. W. and Yarrow. D. [Yeasts:Characteristics and identification] Second edition, Cambridge University Press)

| | |
|---|---|
| Morphology of vegetative cell | spherical, ellipsoidal, cylindrical |
| Form of multiplication | multipolar budding, forming oidia |
| Liquid culture | precipitation and coating were observed (25° C., 3 days) |
| Pseudomycelia | observed (25° C., 3 days) |
| Hyphae | observed (corn meal agar plate culture, 25° C., 3 days) |
| Oidia | observed (corn meal agar plate culture, 25° C., 3 days) |
| Ascospores | not observed on Adams, Gorodkowa, malt, YM, V-8 and potato dextrose media) |
| Fermentation of glucose | negative |
| Assimilation of inositol | positive |
| Assimilation of nitrate | negative |
| Decomposition of urea | negative (not typical form) |
| Coloration of DBB | positive |
| Xylose in cell wall | positive |

Figure 5:
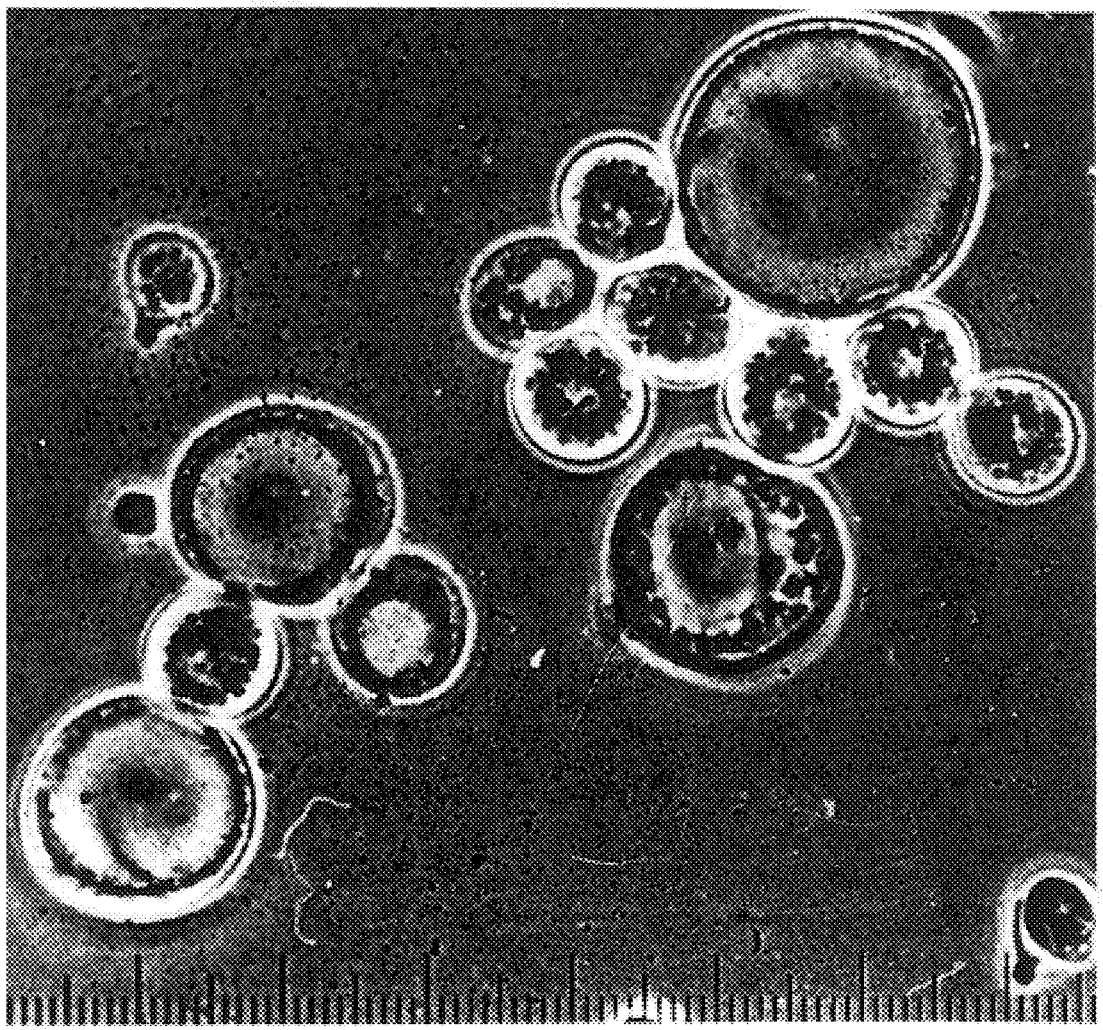
FIG. 5 is a photograph showing the yeast-like microorganism, taken by an optical microscope at a magnitude of 1500.
Figure 6:
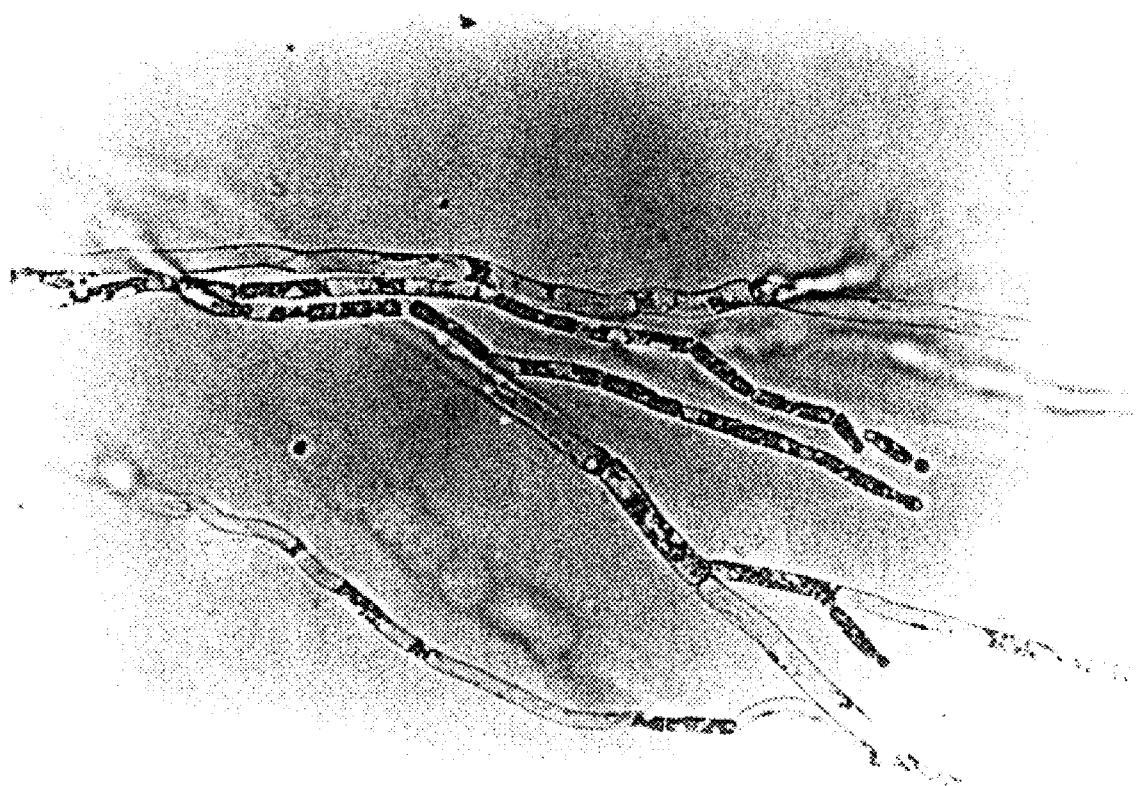
FIG. 6 is a photograph showing hyphae and oidia (at a magnitude of 470) formed after cultivating the yeast-like microorganism of FIG. 5 on a corn meal agar plate at 25° C. for 3 days.

FIG. 5 shows a photograph of the yeast-like microorganism, taken by an optical microscope (at a magnitude of 1500). FIG. 6 is a photograph showing its hyphae and oidia observed after cultivating the microorganism on a corn meal agar plate medium at 25° C. for 3 days, taken by an optical microscope (at a magnitude of 470).

(Identification of the Bacterium)
(Arthrobacter FERM BP-6444)

The bacterium was identified to belong to Arthrobacter, based on its morphology, physiological properties, celluler components, and a GC content: (Sneath P. H. A., Mair, N. S., Sharpe M. E. and Holt J. G. [Bergey's Manual of Systematic Bacteriology] Vol. 2, 1986, Wiliams and Wilkins: Holt J. G., Krieg N. R., Sneath P. H. A., Stanley, J. T. and Wiliams, S. T. [Bergey's Manual of Determinative Bacteriology] ninth edition, 1994, Wiliams and Wilkins).

Arthrobacter belongs to an asporogenic gram-positive rod bacteria showing polymorphism.

| | |
|---|---|
| Morphology | polymorphic rod bacteria |
| Gram stain | positive |
| Spores | negative |
| Motility | positive |
| Relation to oxygen | aerobic |
| Oxidase | negative |
| Catalase | positive |
| OF | negative |
| Resistance to acidity | negative |
| Color of colony | not forming characteristic pigments |
| Rod coccus cycle | positive |
| Elongation of peripheral cells in colony | negative |
| Cell wall | |
| Diamino acid | lysine |
| Acyl-type | acetyl-type |
| Arabino-galactan polymer (assumed using acidic hydrolysis products of the whole cell) | negative |
| Main quinone series | MK-9 (H2) |
| GC content in the DNA (mole percent: measured by HPLC method) | 65 |

Figure 7:
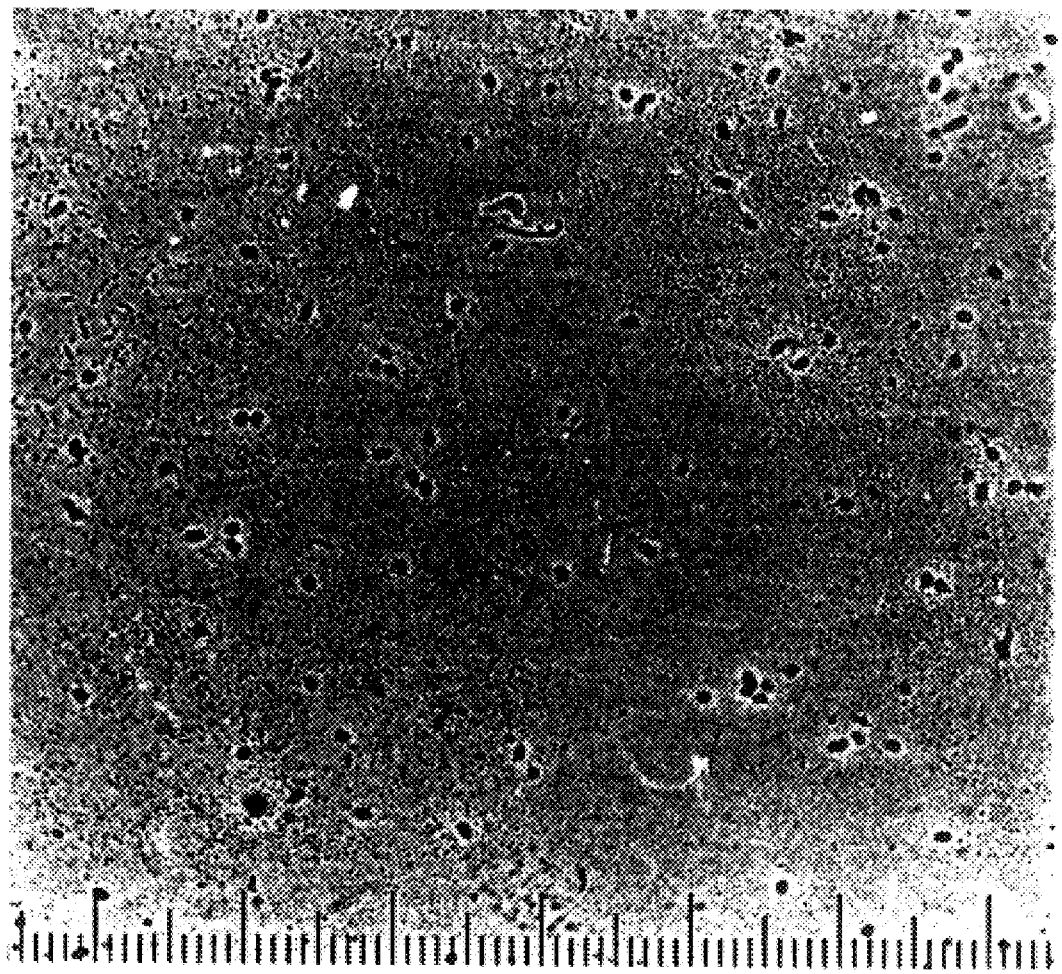
FIG. 7 is a photograph showing the bacterium having the activity of decomposing a polyester containing an aromatic moiety, taken by an optical microscope at a magnitude of 1500.
Figure 8:
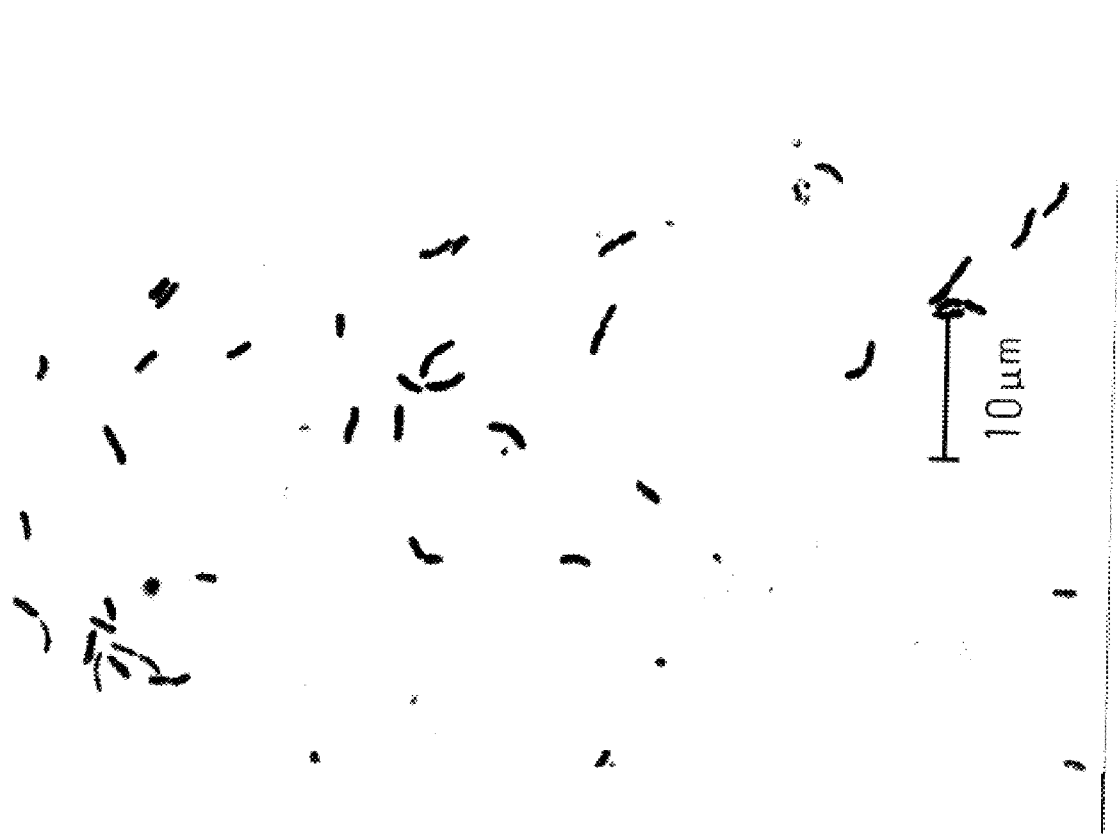
FIG. 8 is a photograph showing the bacterium of FIG. 7 after cultivating it for 8 hours.
Figure 9:
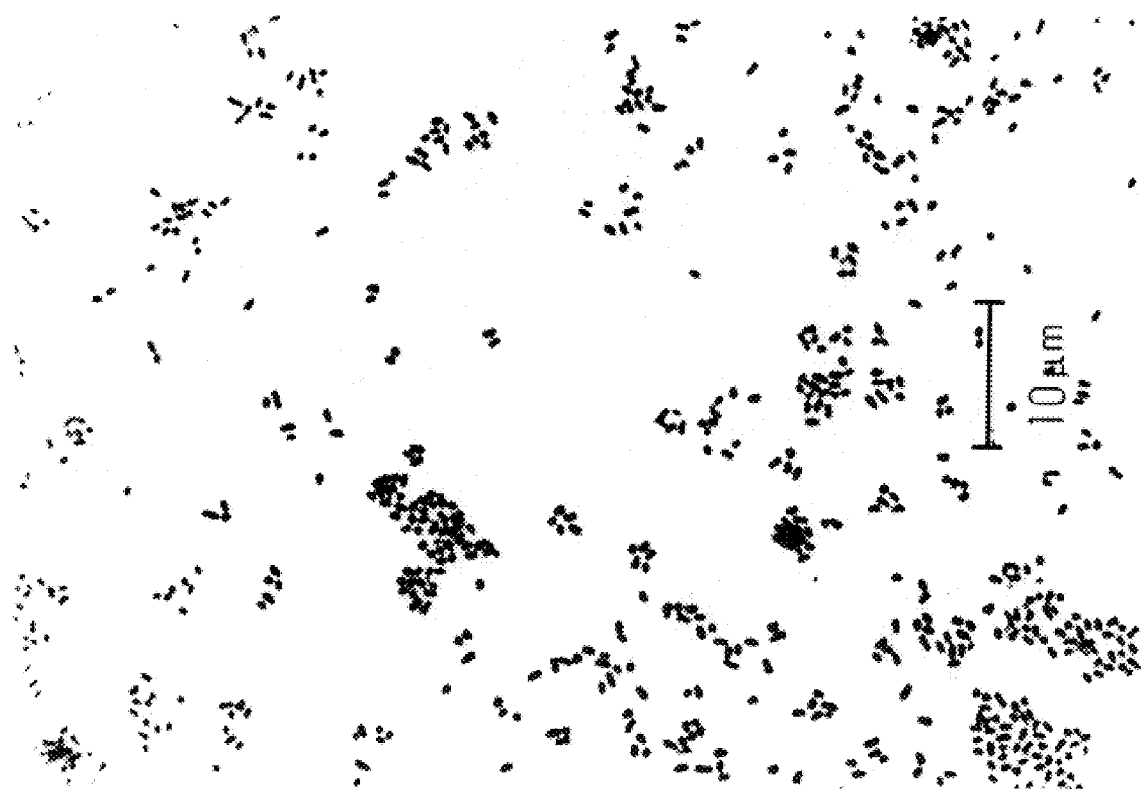
FIG. 9 is a photograph showing the bacterium of FIG. 7 after cultivating it for 72 hours.

FIG. 7 is a photograph showing the bacterium, taken by an optical microscope (at a magnitude of 1500). FIG. 8 shows the bacterium after cultivating it in EYGA medium at 30° C. for 8 hours, and FIG. 9 after 72 hours.

(Denier-reduction Treatment of a Cloth Made of Polyester-fibers Containing Aromatic Moieties)

Cloths made of polyethylene terephthalate were reduced by contacting them with the yeast-like microorganism or bacterium, using the above described medium samples used for screening.

In experiment A, a cloth made of crystalline polyethylene terephthalate fibers, with a dimension of 18 mm×18 mm and a weight of 2.083 gram, was dipped in the above medium, to which the yeast-like microorganism was inoculated. Then, it was cultured for 55 days at 30° C., with its medium replaced every 2 weeks. After the cultivation, the cloth was taken out from the liquid culture and weighed. Experiments B and C were also performed, except that the bacterium was added instead of the yeast-like microorganism in the experiment B and both were added in the experiment C.

As a result, the weight of the cloth was reduced to 1.753 gram in the experiment A, reducing 15.8 percent of its original weight. The weight of the cloth was reduced to 1.751 gram in the experiment B, reducing 15.9 percent of its original weight. The weight of the cloth was reduced to 1.729 gram in the experiment C, reducing 17.0 percent of its original weight. Moreover, fitting and appearance were improved when observed by eyes, and the handling was considerably changed.

What is claimed is:

1. A method for decomposing a polyester containing an aromatic moiety, wherein the polyester is a homopolymer or copolymer of a monomer selected from the group consisting of an alkylene terephthalate, an alkylene phthalate, and an alkylene isophthalate the method comprising: contacting a microorganism, having activity for decomposing a polyester containing an aromatic moiety and ability to utilize polyester as a sole compound, said microorganism comprising one selected from the group consisting of Trichosporon and Arthrobacter, with said polyester to decompose it.

2. The method of claim 1, wherein said Trichosporon is FERM BP-6445.

3. The method of claim 1 said Arthrobacter is FERM BP-6444.

4. The method as claimed in claim 1, wherein the polyester is decomposed by contacting it with Trichosporon FERM BP-6445 and Arthrobacter FERM BP-6444.

5. The method as claimed in claim 1, wherein the alkylene terphthalate is selected from the group consisting of ethylene terephthalate, propylene terphthalate, and butylene terephalate.

6. A method for descomposing a polyester containing aromatic moiety, the method comprising: containing a microorganism, having activity for decomposing a polyester containing an aromatic moiety and ability to utilize polyester as a sole compound, with the polyester to descomposed it, said microorganism comprising at least one of the group consisting of Trichosporon FERM BP-6445 and Arthrobacter FERM BP-6444.

* * * * *